US012799512B2

(12) United States Patent
Ma et al.

(10) Patent No.: US 12,799,512 B2
(45) Date of Patent: Nov. 17, 2026

(54) PREPARATION METHOD FOR AND APPLICATION OF IMMOBILIZED CELLS FOR MANNOSE PRODUCTION

(71) Applicant: Tianjin Yeahe Biotechnology Co., Ltd, Tianjin (CN)

(72) Inventors: Yanhe Ma, Tianjin (CN); Ting Shi, Tianjin (CN); Pingping Han, Tianjin (CN)

(73) Assignee: TIANJIN YEAHE BIOTECHNOLOGY CO., LTD, Tianjin (CN)

( * ) Notice: Subject to any disclaimer, the term of this patent is extended or adjusted under 35 U.S.C. 154(b) by 431 days.

(21) Appl. No.: 18/576,341

(22) PCT Filed: Jan. 4, 2022

(86) PCT No.: PCT/CN2022/070091
§ 371 (c)(1),
(2) Date: Jan. 3, 2024

(87) PCT Pub. No.: WO2023/279687
PCT Pub. Date: Jan. 12, 2023

(65) Prior Publication Data

US 2024/0309414 A1 Sep. 19, 2024

(30) Foreign Application Priority Data

Jul. 5, 2021 (CN) ........................ 202110757694.3

(51) Int. Cl.
*C12P 19/02* (2006.01)
*C12N 11/14* (2006.01)

(52) U.S. Cl.
CPC ............. *C12P 19/02* (2013.01); *C12N 11/14* (2013.01)

(58) Field of Classification Search
None
See application file for complete search history.

(56) References Cited

U.S. PATENT DOCUMENTS 5,240,717 A 8/1993 Takasaki et al.

FOREIGN PATENT DOCUMENTS

| | | |
|---|---|---|
| CN | 107400667 A | 11/2017 |
| CN | 109750011 A | 5/2019 |
| CN | 112342179 A | 2/2021 |
| CN | 113249372 A | 8/2021 |

OTHER PUBLICATIONS

European Patent Office, Extended European Search Report for EP Patent Application No. 22836447.7, dated Feb. 9, 2026, DE.
International Searching Authority, International Search Report, International Application No. PCT/CN2022/070091, dated Apr. 8, 2022, CN.
International Searching Authority, Written Opinion of the International Searching Authority, International Application No. PCT/CN2022/070091, dated Apr. 8, 2022, CN.

*Primary Examiner* — Robert J Yamasaki
*Assistant Examiner* — Charles Zoltan Constantine
(74) *Attorney, Agent, or Firm* — HOWARD M COHN and Associates, LLC

(57) ABSTRACT

A method for preparing immobilized cells for producing mannose, and a method using same for producing mannose, comprising: fermenting to separately obtain fermentation broths of *Escherichia coli* or *Bacillus subtilis* expressing α-glucan phosphorylase, phosphoglucomutase, glucose phosphoisomerase, mannose-6-phosphate isomerase and mannose-6-phosphate phosphatase, and mixing the fermentation broths to obtain a mixed fermentation broth.

14 Claims, 3 Drawing Sheets

Specification includes a Sequence Listing.

PREPARATION METHOD FOR AND APPLICATION OF IMMOBILIZED CELLS FOR MANNOSE PRODUCTION

PRIORITY

The present application is related to, and claims the priority benefit of, and is a 35 U.S.C. 371 national stage application of, International Patent Application Serial No. PCT/CN2022/070091, filed Jan. 4, 2022, which is related to, and claims the priority benefit of Chinese Patent Application No. 202110757694.3, filed Jul. 5, 2021. The contents of each of the aforementioned applications are hereby incorporated by reference in their entireties into this disclosure.

FIELD OF THE INVENTION

The present disclosure relates to the technical field of bioengineering, in particular to the field of mannose production or preparation.

BACKGROUND OF THE INVENTION

Mannose as a sugar having six carbons is an isomer of glucose. It has many functions such as modulating the immunity system, protecting from bacterial or viral infections, promoting glycoprotein synthesis in vivo, and helping control a cancer. Accordingly, mannose is widely used in the fields of biology and medicine. It can serve as a raw material for the synthesis of certain pharmaceuticals or chemicals and in particular precursors of certain important carbohydrate-based pharmaceuticals. It can also be used as a sweetener for food or beverages. In recent years, the need for mannose has been increasing significantly in the fields of functional food, feed additives and medicines. Thus, the development of mannose has a great economic potential.

In most industrial cases, mannose is produced by using the extraction method or the isomerization method. The extraction method mainly uses a coconut shell or an ivory-nut palm seed or the like as a raw material to obtain a mixed sugar solution containing mannose through acidic hydrolysis. In this method, the raw material comprises a plurality of components, resulting in a high cost for the required separation and purification processes; and the use of a large amount of dilute acids and organic solvents can cause environmental pollution and other problems. (Fan, S.-P., et al., High yield production of sugars from deproteinated palm kernel cake under microwave irradiation via dilute sulfuric acid hydrolysis. Bioresource Technology, 2014. 153(0): 69-78. Saari, P. and M. Hurme, Process Synthesis Principles in the Chromatographic Separation of Sugars from Biomass Hydrolysates. Chemical Engineering & Technology, 2011. 34(2): 282-288.) The isomerization method mainly uses glucose or fructose as a raw material and prepares mannose through chemical or enzymatic isomerization. In this method, due to the limitation from thermodynamics, the conversion rate is low, and the separation process is complicated. (Kockritz, A., et al., Rearrangement of glucose to mannose catalyzed by polymer-supported Mo catalysts in the liquid phase. Applied Catalysis A: General, 2008. 334 (1-2): 112-118. Park, C. S., et al., Mannose production from fructose by free and immobilized D-lyxose isomerases from *Providencia stuartii*. Biotechnol Lett, 2010. 32(9) 1305-1309.)

A new method for preparing mannose through biosynthesis was disclosed by Tianjin Institute of Industrial Biotechnology, Chinese Academy of Sciences discloses in its patent CN109750011A. In this method, a multi-enzyme reactor system was built to convert a low-cost carbon source (for example, formaldehyde, glycerin, starch, maltodextrin, sucrose, and glucose) into mannose, which represented a fundamental change from the existing mannose production processes. This multi-enzymes-based mannose synthesis route overcame the disadvantages with the extraction method for synthesizing mannose, including high energy consumption, complex products, difficulties in purification, a number of side reactions, and heavy chemical pollution. It also addressed the defects with the isomerization method, including a low conversion rate and a complicated separation process. However, the multi-enzymes used in this method needed to be extracted from the enzyme-containing cells obtained through fermentation, wherein the extraction mainly included a series of steps such as cell collection, resuspension, homogenization, collection of a supernatant, and enzyme separation and purification. This made enzyme production complicated and also made large-scale production more difficult to achieve. In addition, as the free enzymes and the reaction solution formed a homogeneous mixture, the enzyme could hardly be recycled after the catalytic reaction was completed, which resulted in a low enzyme recycling rate and a high cost for producing enzymes. Due to these problems, the production cost with this method for preparing mannose through biosynthesis could not be further reduced to achieve production on an industrial scale.

A method for producing tagatose by catalyzing starch with a whole cell of *Bacillus subtilis* was reported by Tianjin Institute of Industrial Biotechnology, Chinese Academy of Sciences in its granted patent CN112342179B. This method immobilized the permeabilized *Bacillus subtilis* cell to obtain an immobilized whole cell, and then used the cell to produce tagatose. It achieved recycling of the whole cell and thus reduced the production cost. However, the analysis from researches showed that this method still had some shortcomings in preparing immobilized cells. Firstly, this method required a plurality of steps such as cell collection, resuspension, and permeabilization before immobilization. Secondly, this method used a permeabilized cell for granulation and immobilization, wherein the permeabilization of the cell could easily cause leakage of a heterologous protein expressed in the cell, which led to the loss of the heterologous protein and reduction of enzyme immobilization efficiency during the immobilization process. Thirdly, the method obtained the immobilized enzyme particle by simply extruding to achieve granulation, and thus the obtained particle was not of a uniform size.

Therefore, there is an urgent need to develop a method to obtain an immobilized cell of a uniform size in a simple and convenient way. This method should simplify the process of producing enzymes and avoid or reduce the enzyme leakage or loss during immobilization of a permeable cell to improve the enzyme immobilization efficiency. It should also achieve enzyme recycling to further reduce the mannose production cost and enable the mannose production on an industrial scale.

SUMMARY OF THE INVENTION

Problem to be Solved by the Invention

The existing methods for producing mannose through catalysis with multi-enzymes have many problems, for example, a plurality of steps for producing enzymes, complicated separation and purification processes, a low enzyme recycling rate, and difficulties in recycling enzymes, which lead to a high production cost. In view of these problems, an object of the present disclosure is to provide a method for producing mannose with immobilized cells. It simplifies the steps for producing enzymes and facilitates the separation and purification of the product from the enzymes during mannose production. It achieves recycling of the multiple enzymes used in the new route for preparing mannose with multi-enzymes, reduces the mannose production cost and enables mannose production on an industrial scale.

Solutions to Problems

In order to solve the above technical problems, the present disclosure adopts the following technical solution:

A method for preparing immobilized cells for mannose production, characterized in that the method comprises the steps of:

- fermenting to obtain fermentation broths comprising an *Escherichia coli* or *Bacillus subtilis* expressing α-glucan phosphorylase, phosphoglucomutase, phosphoglucose isomerase, mannose 6-phosphate isomerase, or mannose 6-phosphate phosphatase respectively, and mixing the above fermentation broths to obtain a fermentation mixture;
- adding an inorganic soil to the fermentation mixture, and stirring homogeneously;
- further adding a flocculant to the fermentation mixture to flocculate bacteria, and then adding a cross-linking agent for cross-linking;
- filtering under vacuum to obtain a filter cake, extruding the filter cake to granulate into a strip with a rotary granulator, and then breaking into particles having a uniform length with a spherical shot blasting machine; and
- subjecting the resulting particles to drying by boiling to obtain the immobilized cells for mannose production.

In an embodiment, the present disclosure adopts the following technical solution:

A method for preparing immobilized cells for mannose production, characterized in that the method comprises the steps of:

- fermenting to obtain fermentation broths comprising an *Escherichia coli* or *Bacillus subtilis* expressing α-glucan phosphorylase, phosphoglucomutase, phosphoglucose isomerase, mannose 6-phosphate isomerase, or mannose 6-phosphate phosphatase respectively, and mixing the above fermentation broths to obtain a fermentation mixture;
- adding 1-10% w/v of an inorganic soil to the fermentation mixture, and stirring homogeneously;
- further adding 0.1-2% w/v of a flocculant to the fermentation mixture to flocculate bacteria, and then adding 0.05-3% v/v of a cross-linking agent for cross-linking for 1-4 hours;
- filtering under vacuum to obtain a filter cake, extruding the filter cake to granulate into a strip with a rotary granulator, and then breaking into particles having a uniform length with a spherical shot blasting machine; and
- subjecting the resulting particles to drying by boiling to obtain the immobilized cells for mannose production, wherein the temperature at an air inlet for the boiling drying is controlled at 60-90 °C.

The fermentation broths are prepared by a method known in the art. The fermenting can be carried out using any culture medium for exogenous protein expression, including but not limited to LB medium, SR medium, or TB medium.

Preferably, the α-glucan phosphorylase, the phosphoglucomutase, the phosphoglucose isomerase, the mannose 6-phosphate isomerase, or the mannose 6-phosphate phosphatase is thermostable α-glucan phosphorylase, thermostable phosphoglucomutase, thermostable phosphoglucose isomerase, thermostable mannose 6-phosphate isomerase, or thermostable mannose 6-phosphate phosphatase respectively.

The thermostable α-glucan phosphorylase refers to an enzyme having the function of phosphorylating starch into glucose-1-phosphate (G1P) at 40 °C or above, 45 °C or above, 50 °C or above, 55 °C or above, 60 °C or above, 65 °C or above, 70 °C or above, 75 °C or above, or 80 °C or above. Further preferably, the thermostable α-glucan phosphorylase is derived from a thermophilic microorganism, for example, *Geobacillus kaustophilus, Geobacillus stearothermophilus, Thermotoga maritima, Pseudothermotoga thermarum, Thermococcus kodakarensis, Archaeoglobus fulgidus, Thermoanaerobacter indiensis, Dictyoglomus thermophilum, Caldicellulosiruptor kronotskyensis, Clostridium thermocellum, Caldilinea aerophila, Pyrococcus furiosus, Thermus thermophilus, Methanothermobacter marburgensis*, or *Archaeoglobus profundus*; or the thermostable α-glucan phosphorylase has an amino acid sequence which is at least 70%, preferably at least 80%, more preferably at least 90%, or most preferably at least 95% identical to that of the thermostable α-glucan phosphorylase derived from the thermophilic microorganism. More preferably, the thermostable α-glucan phosphorylase is derived from *Thermococcus kodakarensis.*

Specifically, the thermostable phosphoglucomutase refers to an enzyme having the function of translocating glucose-1-phosphate (G1P) into glucose-6-phosphate (G6P) at 40 °C or above, 45 °C or above, 50 °C or above, 55 °C or above, 60 °C or above, 65 °C or above, 70 °C or above, 75 °C or above, or 80 °C or above. Further preferably, the thermostable phosphoglucomutase is derived from a thermophilic microorganism, for example, *Geobacillus kaustophilus, Geobacillus stearothermophilus, Thermotoga maritima, Pseudothermotoga thermarum, Thermococcus kodakarensis, Archaeoglobus fulgidus, Thermoanaerobacter indiensis, Dictyoglomus thermophilum, Caldicellulosiruptor kronotskyensis, Clostridium thermocellum, Caldilinea aerophila, Pyrococcus furiosus, Thermus thermophilus, Methanothermobacter marburgensis*, or *Archaeoglobus profundus*; or the thermostable phosphoglucomutase has an amino acid sequence which is at least 70%, preferably at least 80%, more preferably at least 90%, or most preferably at least 95% identical to that of the thermostable phosphoglucomutase derived from the thermophilic microorganism. More preferably, the thermostable phosphoglucomutase is derived from *Thermococcus kodakarensis.*

Specifically, the thermostable phosphoglucose isomerase refers to an enzyme having the function of translocating glucose-6-phosphate (G6P) into fructose-6-phosphate (F6P) at 40 °C or above, 45 °C or above, 50 °C or above, 55 °C or above, 60 °C or above, 65 °C or above, 70 °C or above, 75 °C or above, or 80 °C or above. Further preferably, the thermostable phosphoglucose isomerase is derived from a thermophilic microorganism, for example, *Geobacillus kaustophilus, Geobacillus stearothermophilus, Thermotoga maritima, Pseudothermotoga thermarum, Thermococcus kodakarensis, Archaeoglobus fulgidus, Thermoanaerobacter indiensis, Dictyoglomus thermophilum, Caldicellulosiruptor kronotskyensis, Clostridium thermocellum, Caldi-*

*linea aerophila, Pyrococcus furiosus, Thermus thermophilus, Methanothermobacter marburgensis*, or *Archaeoglobus profundus*; or the thermostable phosphoglucose isomerase has an amino acid sequence which is at least 70%, preferably at least 80%, more preferably at least 90%, or most preferably at least 95% identical to that of the thermostable phosphoglucose isomerase derived from the thermophilic microorganism. More preferably, the thermostable phosphoglucose isomerase is derived from *Thermus thermophilus*.

Specifically, the thermostable mannose 6-phosphate isomerase refers to an enzyme having the function of translocating fructose-6-phosphate (F6P) into mannose 6-phosphate (M6P) at 40 °C or above, 45 °C or above, 50 °C or above, 55 °C or above, 60 °C or above, 65 °C or above, 70 °C or above, 75 °C or above, or 80 °C or above. Further preferably, the thermostable mannose 6-phosphate isomerase is derived from a thermophilic microorganism, for example, *Geobacillus kaustophilus, Geobacillus stearothermophilus, Thermotoga maritima, Pseudothermotoga thermarum, Thermococcus kodakarensis, Archaeoglobus fulgidus, Thermoanaerobacter indiensis, Dictyoglomus thermophilum, Caldicellulosiruptor kronotskyensis, Clostridium thermocellum, Caldilinea aerophila, Pyrococcus furiosus, Thermus thermophilus, Methanothermobacter marburgensis*, or *Archaeoglobus profundus*; or the thermostable mannose 6-phosphate isomerase has an amino acid sequence which is at least 70%, preferably at least 80%, more preferably at least 90%, or most preferably at least 95% identical to that of the thermostable mannose 6-phosphate isomerase derived from the thermophilic microorganism. More preferably, the thermostable mannose 6-phosphate isomerase is derived from *Geobacillus thermodenitrificans*.

Specifically, the thermostable mannose 6-phosphate phosphatase refers to an enzyme having the function of removing a phosphate group of mannose-6-phosphate (M6P) to produce mannose at 40 °C or above, 45 °C or above, 50 °C or above, 55 °C or above, 60 °C or above, 65 °C or above, 70 °C or above, 75 °C or above, or 80 °C or above. Further preferably, the thermostable mannose 6-phosphate phosphatase is derived from a thermophilic microorganism, for example, *Geobacillus kaustophilus, Geobacillus stearothermophilus, Thermotoga maritima, Pseudothermotoga thermarum, Thermococcus kodakarensis, Archaeoglobus fulgidus, Thermoanaerobacter indiensis, Dictyoglomus thermophilum, Caldicellulosiruptor kronotskyensis, Clostridium thermocellum, Caldilinea aerophila, Pyrococcus furiosus, Therms thermophilus, Methanothermobacter marburgensis*, or *Archaeoglobus profundus*; or the thermostable mannose 6-phosphate phosphatase has an amino acid sequence which is at least 70%, preferably at least 80%, more preferably at least 90%, or most preferably at least 95% identical to that of the thermostable mannose 6-phosphate phosphatase derived from the thermophilic microorganism. More preferably, the thermostable mannose 6-phosphate phosphatase is derived from *Thermotoga maritima*.

Further preferably, the wet bacteria expressing the thermostable α-glucan phosphorylase, the thermostable phosphoglucomutase, the thermostable phosphoglucose isomerase, the thermostable mannose 6-phosphate isomerase, and the thermostable mannose 6-phosphate phosphatase respectively are mixed in a ratio of (0.1-10):(0.1-10):(0.1-10):(0.1-10):(0.1-10), and the bacteria suspension obtained by mixing has an OD600 of 10-150.

Further, the inorganic soil includes but is not limited to montmorillonite, diatomite, kaolin or bentonite; preferably, the inorganic soil is diatomite.

Further, the flocculant includes but is not limited to polyethyleneimine, chitosan, poly(diallyldimethylammonium chloride) (PDADMAC), or polyacrylamide; preferably, the flocculant is polyethyleneimine or PDADMAC; preferably, the polyethyleneimine has a molecular weight of 600-70,000.

Further, the cross-linking agent includes but is not limited to glutaraldehyde, tris(hydroxymethyl)phosphine, N,N-methylenebisacrylamide, or epichlorohydrin; preferably, the cross-linking agent is glutaraldehyde.

The method further comprises a step of sieving the obtained immobilized cells to obtain morphologically uniform immobilized cells.

Accordingly, the present disclosure also provides a method for producing mannose with an immobilized cell, characterized in that the method comprises converting starch or a starch derivative into mannose with the above immobilized cells.

Further, after the reaction is completed, a step of filtering and recovering the immobilized cell is also included.

In an embodiment, the reaction system for biological conversion comprises 50-300 g/L of starch or starch derivative, a buffer at pH 5.0-8.0, 10-50 mM inorganic phosphate, 3-7 mM divalent magnesium ions, and the immobilized cell.

Further, the buffer can be an HEPES buffer, a phosphate buffer, a Tris buffer, or an acetate buffer, or the like. The inorganic phosphate can be sodium phosphate or potassium phosphate.

Effects of the Invention

Compared with the prior art, the present disclosure has the following beneficial effects. Compared with the use of multi-enzymes to catalyze reactions in the prior art, the method for producing mannose with immobilized cells simplifies the enzyme producing or preparing process, addresses the difficulties in separating multi-enzymes from the product, and facilitates the separation and purification of the product mannose. The immobilized cells can be separated from the reaction solution simply by filtration. Compared with the use of whole cells to catalyze reactions in the prior art, the present disclosure further simplifies the separation of enzymes from the product, enables the repeated use of enzymes, improves the recycling rate of cells and reduces the mannose production cost. In addition, the recycling of cells reduces the environmental pollution by cutting multiple times of fermentation, and simplifies the operation steps. Importantly, in the present disclosure, after the fermentation broths comprising expressed enzymes are prepared and mixed, the fermentation mixture is directly used for later steps including granulation, saving the steps of collecting bacteria from the fermentation broths and resuspending and permeabilizing the bacteria (since the step of recovering the bacteria from the fermentation broths is omitted, the immobilization process is simplified and the operability of the process is improved; the step of permeabilizing cells is also omitted). As the fermentation mixture is directly used for immobilization, the membranes and the walls of the cells suffer from little damage, and thus the expressed enzymes are seldom leaked after immobilization. As a result, a higher enzyme immobilization efficiency can be obtained. In the present disclosure, after immobilization which results in immobilized cells, a rotary extruding granulator is used to prepare strips with a controllable cross-sectional size, and then a spherical shot blasting machine is used to break the prepared strips into particles having a uniform length. Subsequently, the particles are subjected to drying by boiling at a high temperature (to achieve cell permeabilization), and sieved to obtain immobilized enzyme particles having a uniform size, which can be more effective in mannose production. The granulation process adopted in the present disclosure not only facilitates the subsequent permeabilization and helps ensure the uniformity of the particles, but also enables simpler previous steps in terms of bacteria collection (see the specific process of preparing immobilized cells according to the present disclosure as shown in FIG. 1). Experiments showed that the present disclosure achieved a significant effect. When the immobilized *Bacillus subtilis* of the present disclosure were used to catalyze consecutive rounds of reactions, the initial product yield could reach up to 63%, and even they were used to carry out catalysis for 25 consecutive batches, the product yield could still be maintained at 43%. When the immobilized *Escherichia coli* of the present disclosure were used to catalyze consecutive rounds of reactions, the initial product yield could reach up to 65%, and even they were used to carry out catalysis for 25 consecutive batches, the product yield could still be maintained at 44%.

DETAILED DESCRIPTION OF THE INVENTION

Figure 1:
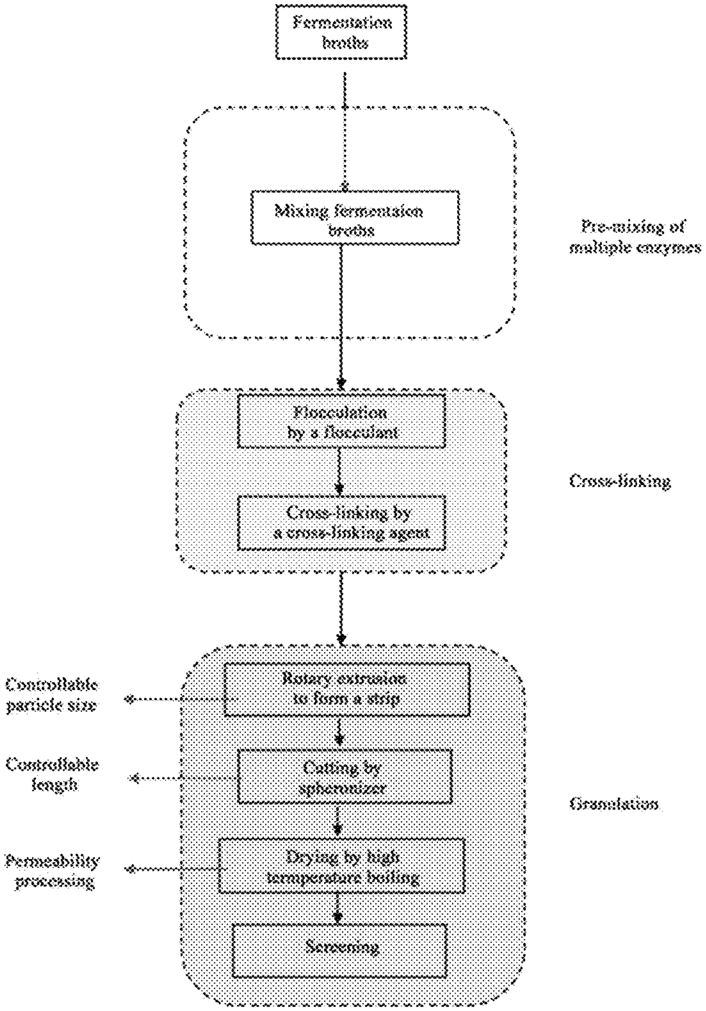
FIG. 1 shows a schematic diagram of a specific process of preparing immobilized cells according to the present disclosure.

In order to further illustrate the technical solutions adopted by the present disclosure and the effects thereof, the technical solutions of the present disclosure are further described through specific Examples below. However, it should be understood that the described Examples are exemplary only and do not pose any limitation to the scope of the present disclosure. It is understood by one skilled in the art that the details and forms of the technical solutions of the present disclosure can be modified or substituted without departing from the spirit and scope of the present disclosure, and these modifications or substitutions fall within the protection scope of the present disclosure.

Example 1: Preparation of Fermentation Broths Comprising *Bacillus subtilis* Expressing Enzyme (1) Construction of pMA5-Pylb-aGP In this Example, the sequence of the agp gene encoding the thermostable α-glucan phosphorylase (NCBI-ProteinlD: BAD85595) was synthesized and spliced into a common plasmid by Suzhou Genewiz Biotechnology Co., Ltd. The agp gene was obtained by PCR using a pair of primers (1-IF and 1-IR). The pMA5-Pylb linear backbone was obtained by PCR using another pair of primers (1-VF and 1-VR). Then, the thermostable α-glucan phosphorylase gene fragment and the pMA5-Pylb vector backbone were assembled by POE-PCR. The product obtained through ligation was transferred into a competent SCK6 cell using the calcium chloride method. A transformant was selected and subjected to colony PCR, identification via double enzyme digestion and sequence verification to obtain an expression vector, which was named pMA5-Pylb-aGP.

```
1-IF:
                                      (SEQ ID NO: 1)
AGAAACAACAAAGGGGGAGATTTGTatggtgaacgtttccaatgccgttg

1-IR:
                                      (SEQ ID NO: 2)
gcttgagctcgactctagaggatcctcagtcaagtcccttccacttgacca

1-VF:
                                      (SEQ ID NO: 3)
tggtcaagtggaagggacttgactgaggatcctctagagtcgagctcaagc

1-VR:
                                      (SEQ ID NO: 4)
caacggcattggaaacgttcaccatACAAATCTCCCCCTTTGTTGTTTCT
```

(2) Construction of pMA5-Pylb-PGM

In this Example, the sequence of the pgm gene encoding the thermostable phosphoglucomutase (NCBI-ProteinID: BAD85297) was synthesized and spliced into a common plasmid by Suzhou Genewiz Biotechnology Co., Ltd. The pgm gene was obtained by PCR using a pair of primers (2-IF and 2-IR). The pMA5-Pylb linear backbone was obtained by PCR using another pair of primers (2-VF and 2-VR). Then, the thermostable phosphoglucomutase gene fragment and the pMA5-Pylb vector backbone were assembled by POE-PCR. The product obtained through ligation was transferred into a competent SCK6 cell using the calcium chloride method. A transformant was selected and subjected to colony PCR, identification via double enzyme digestion and sequence verification to obtain an expression vector, which was named pMA5-Pylb-PGM.

```
2-IF:
                                      (SEQ ID NO: 5)
AGAAACAACAAAGGGGGAGATTTGTatgggcaaactgtttggtaccttcg

2-IR:
                                      (SEQ ID NO: 6)
gcttgagctcgactctagaggatccTTAacctttcagtgcttcttccagc

2-VF:
                                      (SEQ ID NO: 7)
gctggaagaagcactgaaaggtTAAggatcctctagagtcgagctcaagct

2-VR:
                                      (SEQ ID NO: 8)
cgaaggtaccaaacagtttgcccatACAAATCTCCCCCTTTGTTGTTTCT
```

(3) Construction of pMA5-Pylb-PGI

In this Example, the sequence of the pgi gene encoding the thermostable phosphoglucose isomerase (NCBI-ProteinID: AAS82052) was synthesized and spliced into a common plasmid by Suzhou Genewiz Biotechnology Co., Ltd. The pgi gene was obtained by PCR using a pair of primers (3-IF and 4-IR). The pMA5-Pylb linear backbone was obtained by PCR using another pair of primers (3-VF and 3-VR). Then, the thermostable phosphoglucose isomerase gene fragment and the pMA5-Pylb vector backbone were assembled by POE-PCR. The product obtained through ligation was transferred into a competent SCK6 cell using the calcium chloride method. A transformant was selected and subjected to colony PCR, identification via double enzyme digestion and sequence verification to obtain an expression vector, which was named pMA5-Pylb-PGI.

```
3-IF:
                                    (SEQ ID NO: 9)
AGAAACAACAAAGGGGGAGATTTGTATGCTGCGTCTGGATACTCGCTTTC

3-IR:
                                   (SEQ ID NO: 10)
agcttgagctcgactctagaggatccTTAACCAGCCAGGCGTTTACGAGTC

3-VF:
                                   (SEQ ID NO: 11)
GACTCGTAAACGCCTGGCTGGTTAAggatcctctagagtcgagctcaagct

3-VR:
                                   (SEQ ID NO: 12)
GAAAGCGAGTATCCAGACGCAGCATACAAATCTCCCCCTTTGTTGTTTCT
```

(4) Construction of pMA5-Pylb-MPI

In this Example, the sequence of the mpi gene encoding the thermostable mannose 6-phosphate isomerase (NCBI-ProteinID: AAS81322) was synthesized and spliced into a common plasmid by Suzhou Genewiz Biotechnology Co., Ltd. The mpi gene was obtained by PCR using a pair of primers (4-IF and 4-IR). The pMA5-Pylb linear backbone was obtained by PCR using another pair of primers (4-VF and 4-VR). Then, the thermostable mannose 6-phosphate isomerase gene fragment and the pMA5-Pylb vector backbone were assembled by POE-PCR. The product obtained through ligation was transferred into a competent SCK6 cell using the calcium chloride method. A transformant was selected and subjected to colony PCR, identification via double enzyme digestion and sequence verification to obtain an expression vector, which was named pMA5-Pylb-MPI.

```
4-IF:
                                   (SEQ ID NO: 13)
GTAGAAACAACAAAGGGGGAGATTTGTatgaggcggttggagcccaaacc
cgtggc

4-VF:
                                   (SEQ ID NO: 14)
ccacgggtttgggctccaaccgcctcatACAAATCTCCCCCTTTGTTGTT
TCTAC

4-VR:
                                   (SEQ ID NO: 15)
tgccgccctggccaaggagggggcgtgaggatcctctagagtcgagctca
agc

4-IR:
                                   (SEQ ID NO: 16)
gcttgagctcgactctagaggatcctcacgccccctccttggccagggcg
gca
```

(5) Construction of pMA5-Pylb-M6PP

In this Example, the sequence of the m6pp gene encoding the thermostable mannose 6-phosphate phosphatase (NCBI-ProteinID: NP_228460) was synthesized and spliced into a common plasmid by Suzhou Genewiz Biotechnology Co., Ltd. The m6pp gene was obtained by PCR using a pair of primers (5-IF and 5-IR). The pMA5-Pylb linear backbone was obtained by PCR using another pair of primers (5-VF and 5-VR). Then, the thermostable mannose 6-phosphate phosphatase gene fragment and the pMA5-Pylb vector backbone were assembled by POE-PCR. The product obtained through ligation was transferred into a competent SCK6 cell using the calcium chloride method. A transformant was selected and subjected to colony PCR, identification via double enzyme digestion and sequence verification to obtain an expression vector, which was named pMA5-Pylb-M6PP.

```
5-IF:
                                   (SEQ ID NO: 17)
GTAGAAACAACAAAGGGGGAGATTTGTATGTACCGCGTTTTTGTTTTTGA
TC

5-VF:
                                   (SEQ ID NO: 18)
GATCAAAAACAAAAACGCGGTACATACAAATCTCCCCCTTTGTTGTTTCT
AC

5-VR:
                                   (SEQ ID NO: 19)
AGCACCGATTGTCTGGATGAAtgaggatcctctagagtcgagctcaagc

5-IR:
                                   (SEQ ID NO: 20)
gcttgagctcgactctagaggatcctcaTTCATCCAGACAATCGGTGCT
```

(6) Preparation of Fermentation Broths

Figure 2:
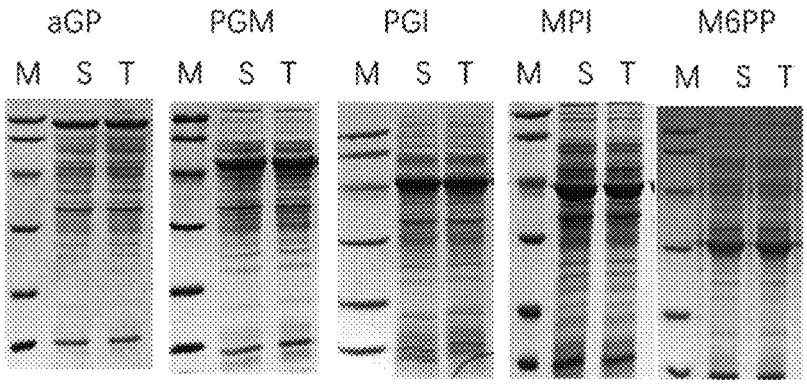
FIG. 2 shows the SDS-PAGE analysis of the various enzymes in Example 1, wherein M indicates the protein marker, S indicates the supernatant of the cell lysate, and T indicates the total protein.

Recombinantly engineered *Bacillus subtilis* strains (SCK6 was selected as the starting strain, see CN112342179B) which expressing a gene of the thermostable α-glucan phosphorylase, a gene of the thermostable phosphoglucomutase, a gene of the thermostable phosphoglucose isomerase, a gene of the thermostable mannose 6-phosphate isomerase, or a gene of the thermostable mannose 6-phosphate phosphatase were selected respectively, inoculated into LB medium respectively, and cultured overnight at 37 °C with shaking. Then the respective culture was transferred to LB medium at an inoculum volume of 1%, and cultured overnight at 37 °C with shaking to obtain a fermentation broth of *Bacillus subtilis* expressing thermostable α-glucan phosphorylase, a fermentation broth of *Bacillus subtilis* expressing thermostable phosphoglucomutase, a fermentation broth of *Bacillus subtilis* expressing thermostable phosphoglucose isomerase, a fermentation broth of *Bacillus subtilis* expressing thermostable mannose 6-phosphate isomerase, and a fermentation broth of *Bacillus subtilis* expressing thermostable mannose 6-phosphate phosphatase, respectively. The analysis of expression of the thermostable α-glucan phosphorylase, the thermostable phosphoglucomutase, the thermostable phosphoglucose isomerase, the thermostable mannose 6-phosphate isomerase, and the thermostable mannose 6-phosphate phosphatase in *Bacillus subtilis* were shown in FIG. 2.

Example 2: Production of Mannose with Immobilized *Bacillus subtilis*

The fermentation broth of *Bacillus subtilis* expressing thermostable α-glucan phosphorylase, the fermentation broth of *Bacillus subtilis* expressing thermostable phosphoglucomutase, the fermentation broth of *Bacillus subtilis* expressing thermostable phosphoglucose isomerase, the fermentation broth of *Bacillus subtilis* expressing thermostable mannose 6-phosphate isomerase, and the fermentation broth of *Bacillus subtilis* expressing thermostable mannose 6-phosphate phosphatase prepared in Example 1 were mixed in a ratio of 1:1:1:1:1 according to OD600, so that the OD600=100. And 2% w/v of montmorillonite was added to the bacteria suspension, and stirred homogeneously. Subsequently, 1% w/v of the aqueous solution of polyethyleneimine having a molecular weight of 600 was added and flocculation was carried out at room temperature. Then, 0.5% v/v of glutaraldehyde aqueous solution was added and cross-linking was carried out at room temperature for 2 hours. Filtration was carried out under vacuum to obtain a filter cake. The filter cake was extruded and thus granulated into strips having a particle size of 3.0 mm with a rotary granulator. Then the strips were broken into particles having a uniform length with a spherical shot blasting machine. The resulting immobilized cell particles were subjected to drying by boiling at 70 °C to obtain immobilized cells.

In a reaction system having a volume of 1 L, starch at a final concentration of 100 g/L, a 50 mM sodium phosphate buffer (pH 7.0) and the immobilized *Bacillus subtilis* were respectively added to achieve OD600=20. Reaction was allowed to carried out in a water bath in a shaker at 70 °C. During reaction, the content of mannose was analyzed by HPLC. After the reaction was completed, the immobilized *Bacillus subtilis* was collected by simple filtration and washed with buffer solution before proceeding to the next batch of reaction. Experimental results showed that when the immobilized *Bacillus subtilis* were used to catalyze consecutive rounds of reactions, the initial product yield reached up to 60%, and as the catalysis was carried out for 20 consecutive batches, the product yield was still maintained at 40%.

Example 3: Production of Mannose with Immobilized *Bacillus subtilis*

The fermentation broth of *Bacillus subtilis* expressing thermostable α-glucan phosphorylase, the fermentation broth of *Bacillus subtilis* expressing thermostable phosphoglucomutase, the fermentation broth of *Bacillus subtilis* expressing thermostable phosphoglucose isomerase, the fermentation broth of *Bacillus subtilis* expressing thermostable mannose 6-phosphate isomerase, and the fermentation broth of *Bacillus subtilis* expressing thermostable mannose 6-phosphate phosphatase prepared in Example 1 were mixed in a ratio of 1:1:1:1:1 according to OD600, so that the OD600=100. And 5% w/v of diatomite was added to the bacteria suspension, and stirred homogeneously. Subsequently, 0.5% w/v of the aqueous solution of polyethyleneimine having a molecular weight of 70,000 was added and flocculation was carried out at room temperature. Then, 0.5% v/v of glutaraldehyde aqueous solution was added and cross-linking was carried out at room temperature for 2 hours. Filtration was carried out under vacuum to obtain a filter cake. The filter cake was extruded and thus granulated into strips having a particle size of 0.4 mm with a rotary granulator. Then the strips were broken into particles having a uniform length with a spherical shot blasting machine. The resulting immobilized cell particles were subjected to drying by boiling at 60 °C to obtain immobilized cells.

Figure 4:
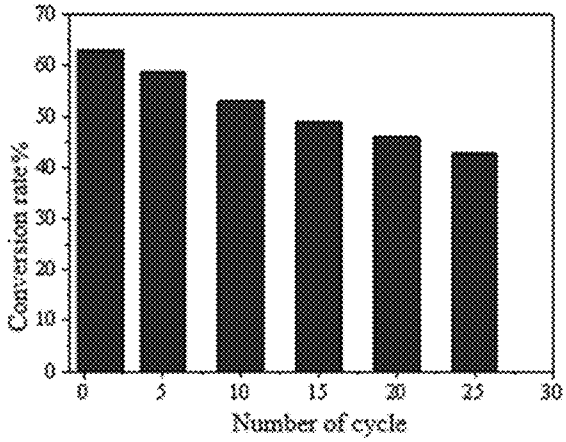
FIG. 4 shows the effect of the immobilized *Bacillus subtilis* in producing mannose in Example 3.

Mannose was produced using the method of Example 2. Experimental results as shown in FIG. 4 demonstrated that when the immobilized *Bacillus subtilis* was used to catalyze consecutive rounds of reactions, the initial product yield reached up to 65%, and as the catalysis was carried out for 25 consecutive batches, the product yield was still maintained at 45%.

Example 4: Production of Mannose with Immobilized *Bacillus Subtilis*

The fermentation broth of *Bacillus subtilis* expressing thermostable α-glucan phosphorylase, the fermentation broth of *Bacillus subtilis* expressing thermostable phosphoglucomutase, the fermentation broth of *Bacillus subtilis* expressing thermostable phosphoglucose isomerase, the fermentation broth of *Bacillus subtilis* expressing thermostable mannose 6-phosphate isomerase, and the fermentation broth of *Bacillus subtilis* expressing thermostable mannose 6-phosphate phosphatase prepared in Example 1 were mixed in a ratio of 1:1:1:1:1 according to OD600, so that the OD600=100. And 2% w/v of diatomite was added to the bacteria suspension, and stirred homogeneously. Subsequently, 0.5% w/v of poly(diallyldimethylammonium chloride) (PDADMAC) aqueous solution was added and flocculation was carried out at room temperature. Then, 0.5% v/v of glutaraldehyde aqueous solution was added and cross-linking was carried out at room temperature for 3 hours. Filtration was carried out under vacuum to obtain a filter cake. The filter cake was extruded and thus granulated into strips having a particle size of 1.0 mm with a rotary granulator. Then the strips were broken into particles having a uniform length with a spherical shot blasting machine. The resulting immobilized cell particles were subjected to drying by boiling at 90 °C to obtain immobilized cells.

Mannose was produced using the method of Example 2. Experimental results showed that when the immobilized *Bacillus subtilis* was used to catalyze consecutive rounds of reactions, the initial product yield reached up to 63%, and as the catalysis was carried out for 25 consecutive batches, the product yield was still maintained at 43%.

Example 5: Production of Mannose with Immobilized *Bacillus subtilis*

The fermentation broth of *Bacillus subtilis* expressing thermostable α-glucan phosphorylase, the fermentation broth of *Bacillus subtilis* expressing thermostable phosphoglucomutase, the fermentation broth of *Bacillus subtilis* expressing thermostable phosphoglucose isomerase, the fermentation broth of *Bacillus subtilis* expressing thermostable mannose 6-phosphate isomerase, and the fermentation broth of *Bacillus subtilis* expressing thermostable mannose 6-phosphate phosphatase prepared in Example 1 were mixed in a ratio of 1:1:1:2:2 according to OD600, so that the OD600=100. And 4% w/v of diatomite was added to the bacteria suspension, and stirred homogeneously. Subsequently, 1% w/v of poly(diallyldimethylammonium chloride) (PDADMAC) aqueous solution was added and flocculation was carried out at room temperature. Then, 1% v/v of glutaraldehyde aqueous solution was added and cross-linking was carried out at room temperature for 3 hours. Filtration was carried out under vacuum to obtain a filter cake. The filter cake was extruded and thus granulated into strips having a particle size of 1.0 mm with a rotary granulator. Then the strips were broken into particles having a uniform length with a spherical shot blasting machine. The resulting immobilized cell particles were subjected to drying by boiling at 70 °C to obtain immobilized cells.

Mannose was produced using the method of Example 2. Experimental results showed that when the immobilized *Bacillus subtilis* was used to catalyze consecutive rounds of reactions, the initial product yield reached up to 63%, and as the catalysis was carried out for 25 consecutive batches, the product yield was still maintained at 40%.

Example 6: Production of Mannose with Immobilized *Bacillus subtilis*

The fermentation broth of *Bacillus subtilis* expressing thermostable α-glucan phosphorylase, the fermentation broth of *Bacillus subtilis* expressing thermostable phosphoglucomutase, the fermentation broth of *Bacillus subtilis* expressing thermostable phosphoglucose isomerase, the fermentation broth of *Bacillus subtilis* expressing thermostable mannose 6-phosphate isomerase, and the fermentation broth of *Bacillus subtilis* expressing thermostable mannose 6-phosphate phosphatase prepared in Example 1 were mixed in a ratio of 1:1:1:1:1 according to OD600, so that the OD600=100. And 6% w/v of diatomite was added to the bacteria suspension, and stirred homogeneously. Subsequently, 0.8% w/v of the aqueous solution of polyethyleneimine having a molecular weight of 70,000 was added and flocculation was carried out at room temperature. Then, 0.5% v/v of tris(hydroxymethyl)phosphine aqueous solution was added and cross-linking was carried out at room temperature for 2 hours. Filtration was carried out under vacuum to obtain a filter cake. The filter cake was extruded and thus granulated into strips having a particle size of 0.4 mm with a rotary granulator. Then the strips were broken into particles having a uniform length with a spherical shot blasting machine. The resulting immobilized cell particles were subjected to drying by boiling at 70 °C to obtain immobilized cells.

Mannose was produced using the method of Example 2. Experimental results showed that when the immobilized *Bacillus subtilis* was used to catalyze consecutive rounds of reactions, the initial product yield reached up to 64%, and as the catalysis was carried out for 25 consecutive batches, the product yield was maintained at 41%.

Example 7: Production of Mannose with Immobilized *Bacillus subtilis*

The fermentation broth of *Bacillus subtilis* expressing thermostable α-glucan phosphorylase, the fermentation broth of *Bacillus subtilis* expressing thermostable phosphoglucomutase, the fermentation broth of *Bacillus subtilis* expressing thermostable phosphoglucose isomerase, the fermentation broth of *Bacillus subtilis* expressing thermostable mannose 6-phosphate isomerase, and the fermentation broth of *Bacillus subtilis* expressing thermostable mannose 6-phosphate phosphatase prepared in Example 1 were mixed in a ratio of 1:1:1:1:1 according to OD600, so that the OD600=100. And 3% w/v of diatomite was added to the bacteria suspension, and stirred homogeneously. Subsequently, 0.5% w/v of polyacrylamide aqueous solution was added and flocculation was carried out at room temperature. Then, 2.0% v/v of N,N-methylenebisacrylamide aqueous solution was added and cross-linking was carried out at room temperature for 2 hours. Filtration was carried out under vacuum to obtain a filter cake. The filter cake was extruded and thus granulated into strips having a particle size of 1.0 mm with a rotary granulator. Then the strips were broken into particles having a uniform length with a spherical shot blasting machine. The resulting immobilized cell particles were subjected to drying by boiling at 90 °C to obtain immobilized cells.

Mannose was produced using the method of Example 2. Experimental results showed that when the immobilized *Bacillus subtilis* was used to catalyze consecutive rounds of reactions, the initial product yield reached up to 65%, and as the catalysis was carried out for 25 consecutive batches, the product yield was maintained at 42%.

Example 8: Production of Mannose with Immobilized *Bacillus subtilis*

The fermentation broth of *Bacillus subtilis* expressing thermostable α-glucan phosphorylase, the fermentation broth of *Bacillus subtilis* expressing thermostable phosphoglucomutase, the fermentation broth of *Bacillus subtilis* expressing thermostable phosphoglucose isomerase, the fermentation broth of *Bacillus subtilis* expressing thermostable mannose 6-phosphate isomerase, and the fermentation broth of *Bacillus subtilis* expressing thermostable mannose 6-phosphate phosphatase prepared in Example 1 were mixed in a ratio of 1:1:1:1:1 according to OD600, so that the OD600=100. And 1% w/v of diatomite was added to the bacteria suspension, and stirred homogeneously. Subsequently, 0.1% w/v of the aqueous solution of polyethyleneimine having a molecular weight of 70,000 was added and flocculation was carried out at room temperature. Then, 0.3% v/v of epichlorohydrin aqueous solution was added and cross-linking was carried out at room temperature for 2 hours. Filtration was carried out under vacuum to obtain a filter cake. The filter cake was extruded and thus granulated into strips having a particle size of 1.0 mm with a rotary granulator. Then the strips were broken into particles having a uniform length with a spherical shot blasting machine. The resulting immobilized cell particles were subjected to drying by boiling at 70 °C to obtain immobilized cells.

Mannose was produced using the method of Example 2. Experimental results showed that when the immobilized *Bacillus subtilis* was used to catalyze consecutive rounds of reactions, the initial product yield reached up to 63%, and as the catalysis was carried out for 25 consecutive batches, the product yield was maintained at 40%.

Example 9: Preparation of Fermentation Broths Comprising *Escherichia coli* Expressing Enzyme A plasmid comprising a gene of the thermostable α-glucan phosphorylase, a gene of the thermostable phosphoglucomutase, a gene of the thermostable phosphoglucose isomerase, a gene of the thermostable mannose 6-phosphate isomerase, or a gene of the thermostable mannose 6-phosphate phosphatase was constructed using the method as described in the patent CN 109750011 A. The respective gene of the thermostable α-glucan phosphorylase, the thermostable phosphoglucomutase, the thermostable phosphoglucose isomerase, the thermostable mannose 6-phosphate isomerase, or the thermostable mannose 6-phosphate phosphatase was directly synthesized between the restriction sites of NdeI and XhoI on the vector pET-21a. The resulting recombinant plasmid was named pET-21a-aGP, pET-21a-PGM, pET-21a-PGI, pET-21a-MPI, or pET-21a-M6PP respectively.

Figure 3:
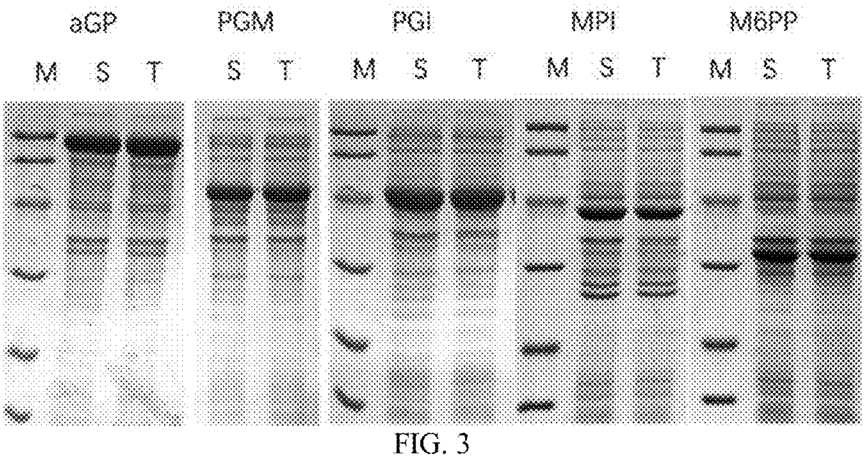
FIG. 3 shows the SDS-PAGE analysis of the various enzymes in Example 9, wherein M indicates the protein marker, S indicates the supernatant of the cell lysate, and T indicates the total protein.

The recombinant plasmids pET-21a-aGP, pET-21a-PGM, pET-21a-PGI, pET-21a-MPI, and pET-21a-M6PP were respectively transferred into the *Escherichia coli* strain BL21 (DE3) to obtain a recombinantly engineered bacteria. Single clones were picked respectively and cultured in the LB medium overnight at 37 °C with shaking. Then the culture was transferred to LB medium at an inoculum volume of 1%, added with IPTG for induction at 18 °C and cultured overnight with shaking to obtain a fermentation broth of *Escherichia coli* expressing thermostable α-glucan phosphorylase, a fermentation broth of *Escherichia coli* expressing thermostable phosphoglucomutase, a fermentation broth of *Escherichia coli* expressing thermostable phosphoglucose isomerase, a fermentation broth of *Escherichia coli* expressing thermostable mannose 6-phosphate isomerase, and a fermentation broth of *Escherichia coli* expressing thermostable mannose 6-phosphate phosphatase, respectively. The analysis of expression of the thermostable α-glucan phosphorylase, the thermostable phosphoglucomutase, the thermostable phosphoglucose isomerase, the thermostable mannose 6-phosphate isomerase, and the thermostable mannose 6-phosphate phosphatase in *Escherichia coli* was shown in FIG. 3.

Example 10: Production of Mannose with Immobilized *Escherichia coli*

The fermentation broth of *Escherichia coli* expressing thermostable α-glucan phosphorylase, the fermentation broth of *Escherichia coli* expressing thermostable phosphoglucomutase, the fermentation broth of *Escherichia coli* expressing thermostable phosphoglucose isomerase, the fermentation broth of *Escherichia coli* expressing thermostable mannose 6-phosphate isomerase, and the fermentation broth of *Escherichia coli* expressing thermostable mannose 6-phosphate phosphatase prepared in Example 9 were mixed in a ratio of 1:1:1:1:1 according to OD600, so that the OD600=100. And 1% w/v of montmorillonite was added to the bacteria suspension, and stirred homogeneously. Subsequently, 0.2% w/v of the aqueous solution of polyethyleneimine having a molecular weight of 600 was added and flocculation was carried out at room temperature. Then, 0.2% v/v of glutaraldehyde aqueous solution was added and cross-linking was carried out at room temperature for 2 hours. Filtration was carried out under vacuum to obtain a filter cake. The filter cake was extruded and thus granulated into strips having a particle size of 0.8 mm with a rotary granulator. Then the strips were broken into particles having a uniform length with a spherical shot blasting machine. The resulting immobilized cell particles were subjected to drying by boiling at 60 °C to obtain immobilized cells.

Mannose was produced using the method of Example 2. Experimental results showed that when the immobilized *Escherichia coli* was used to catalyze consecutive rounds of reactions, the initial product yield reached up to 60%, and as the catalysis was carried out for 20 consecutive batches, the product yield was maintained at more than 40%.

Example 11: Production of Mannose with Immobilized *Escherichia coli*

The fermentation broth of *Escherichia coli* expressing thermostable α-glucan phosphorylase, the fermentation broth of *Escherichia coli* expressing thermostable phosphoglucomutase, the fermentation broth of *Escherichia coli* expressing thermostable phosphoglucose isomerase, the fermentation broth of *Escherichia coli* expressing thermostable mannose 6-phosphate isomerase, and the fermentation broth of *Escherichia coli* expressing thermostable mannose 6-phosphate phosphatase prepared in Example 9 were mixed in a ratio of 1:1:1:1:1 according to OD600, so that the OD600=100. And 1% w/v of diatomite was added to the bacteria suspension, and stirred homogeneously. Subsequently, 0.5% w/v of the aqueous solution of polyethyleneimine having a molecular weight of 70,000 was added and flocculation was carried out at room temperature. Then, 1% v/v of glutaraldehyde aqueous solution was added and cross-linking was carried out at room temperature for 2 hours. Filtration was carried out under vacuum to obtain a filter cake. The filter cake was extruded and thus granulated into strips having a particle size of 1.0 mm with a rotary granulator. Then the strips were broken into particles having a uniform length with a spherical shot blasting machine. The resulting immobilized cell particles were subjected to drying by boiling at 70 °C to obtain immobilized cells.

Figure 5:
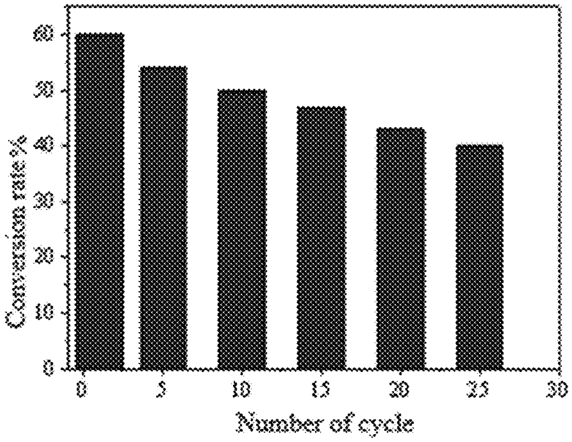
FIG. 5 shows the effect of the immobilized *Escherichia coli* in producing mannose in Example 11.

Mannose was produced using the method of Example 2. Experimental results as shown in FIG. 5 demonstrated that when the immobilized *Escherichia coli* were used to catalyze consecutive rounds of reactions, the initial product yield reached up to 65%, and as the catalysis was carried out for 25 consecutive batches, the product yield was maintained at 44%.

Example 12: Production of Mannose with Immobilized *Escherichia coli*

The fermentation broth of *Escherichia coli* expressing thermostable α-glucan phosphorylase, the fermentation broth of *Escherichia coli* expressing thermostable phosphoglucomutase, the fermentation broth of *Escherichia coli* expressing thermostable phosphoglucose isomerase, the fermentation broth of *Escherichia coli* expressing thermostable mannose 6-phosphate isomerase, and the fermentation broth of *Escherichia coli* expressing thermostable mannose 6-phosphate phosphatase prepared in Example 9 were mixed in a ratio of 1:1:1:1:1 according to OD600, so that the OD600=100. And 2% w/v of diatomite was added to the bacteria suspension, and stirred homogeneously. Subsequently, 0.5% w/v of poly(diallyldimethylammonium chloride) (PDADMAC) aqueous solution was added and flocculation was carried out at room temperature. Then, 0.5% v/v of glutaraldehyde aqueous solution was added and cross-linking was carried out at room temperature for 3 hours. Filtration was carried out under vacuum to obtain a filter cake. The filter cake was extruded and thus granulated into strips having a particle size of 3.0 mm with a rotary granulator. Then the strips were broken into particles having a uniform length with a spherical shot blasting machine. The resulting immobilized cell particles were subjected to drying by boiling at 90 °C to obtain immobilized cells.

Mannose was produced using the method of Example 2. Experimental results showed that when the immobilized *Escherichia coli* was used to catalyze consecutive rounds of reactions, the initial product yield reached up to 60%, and as the catalysis was carried out for 25 consecutive batches, the product yield was maintained at 40%.

Example 13: Production of Mannose with Immobilized *Escherichia coli*

The fermentation broth of *Escherichia coli* expressing thermostable α-glucan phosphorylase, the fermentation broth of *Escherichia coli* expressing thermostable phosphoglucomutase, the fermentation broth of *Escherichia coli* expressing thermostable phosphoglucose isomerase, the fermentation broth of *Escherichia coli* expressing thermostable mannose 6-phosphate isomerase, and the fermentation broth of *Escherichia coli* expressing thermostable mannose 6-phosphate phosphatase prepared in Example 9 were mixed in a ratio of 1:1:1:2:2 according to OD600, so that the OD600=100. And 3% w/v of diatomite was added to the bacteria suspension, and stirred homogeneously. Subsequently, 0.4% w/v of poly(diallyldimethylammonium chloride) (PDADMAC) aqueous solution was added and flocculation was carried out at room temperature. Then, 1% v/v of glutaraldehyde aqueous solution was added and cross-linking was carried out at room temperature for 3 hours. Filtration was carried out under vacuum to obtain a filter cake. The filter cake was extruded and thus granulated into strips having a particle size of 1.0 mm with a rotary granulator. Then the strips were broken into particles having a uniform length with a spherical shot blasting machine. The resulting immobilized cell particles were subjected to drying by boiling at 70 °C to obtain immobilized cells.

Mannose was produced using the method of Example 2. Experimental results showed that when the immobilized *Escherichia coli* were used to catalyze consecutive rounds of reactions, the initial product yield reached up to 60%, and as the catalysis was carried out for 25 consecutive batches, the product yield was maintained at 41%.

Example 14: Production of Mannose with Immobilized *Escherichia coli*

The fermentation broth of *Escherichia coli* expressing thermostable α-glucan phosphorylase, the fermentation broth of *Escherichia coli* expressing thermostable phosphoglucomutase, the fermentation broth of *Escherichia coli* expressing thermostable phosphoglucose isomerase, the fermentation broth of *Escherichia coli* expressing thermostable mannose 6-phosphate isomerase, and the fermentation broth of *Escherichia coli* expressing thermostable mannose 6-phosphate phosphatase prepared in Example 9 were mixed in a ratio of 1:1:1:1:1 according to OD600, so that the OD600=100. And 3% w/v of diatomite was added to the bacteria suspension, and stirred homogeneously. Subsequently, 0.5% w/v of the aqueous solution of polyethyleneimine having a molecular weight of 70,000 was added and flocculation was carried out at room temperature. Then, 1.0% v/v of tris(hydroxymethyl)phosphine aqueous solution was added and cross-linking was carried out at room temperature for 2 hours. Filtration was carried out under vacuum to obtain a filter cake. The filter cake was extruded and thus granulated into strips having a particle size of 1.0 mm with a rotary granulator. Then the strips were broken into particles having a uniform length with a spherical shot blasting machine. The resulting immobilized cell particles were subjected to drying by boiling at 70 °C to obtain immobilized cells.

Mannose was produced using the method of Example 2. Experimental results showed that when the immobilized *Escherichia coli* were used to catalyze consecutive rounds of reactions, the initial product yield reached up to 61%, and as the catalysis was carried out for 25 consecutive batches, the product yield was maintained at 40%.

Example 15: Production of Mannose with Immobilized *Escherichia coli*

The fermentation broth of *Escherichia coli* expressing thermostable α-glucan phosphorylase, the fermentation broth of *Escherichia coli* expressing thermostable phosphoglucomutase, the fermentation broth of *Escherichia coli* expressing thermostable phosphoglucose isomerase, the fermentation broth of *Escherichia coli* expressing thermostable mannose 6-phosphate isomerase, and the fermentation broth of *Escherichia coli* expressing thermostable mannose 6-phosphate phosphatase prepared in Example 9 were mixed in a ratio of 1:1:1:1:1 according to OD600, so that the OD600=100. And 5% w/v of diatomite was added to the bacteria suspension, and stirred homogeneously. Subsequently, 0.8% w/v of polyacrylamide aqueous solution was added and flocculation was carried out at room temperature. Then, 0.8% v/v of N,N-methylenebisacrylamide aqueous solution was added and cross-linking was carried out at room temperature for 2 hours. Filtration was carried out under vacuum to obtain a filter cake. The filter cake was extruded and thus granulated into strips having a particle size of 1.0 mm with a rotary granulator. Then the strips were broken into particles having a uniform length with a spherical shot blasting machine. The resulting immobilized cell particles were subjected to drying by boiling at 90 °C to obtain immobilized cells.

Mannose was produced using the method of Example 2. Experimental results showed that when the immobilized *Escherichia coli* was used to catalyze consecutive rounds of reactions, the initial product yield reached up to 63%, and as the catalysis was carried out for 25 consecutive batches, the product yield was maintained at 41%.

Example 16: Production of Mannose with Immobilized *Escherichia coli*

The fermentation broth of *Escherichia coli* expressing thermostable α-glucan phosphorylase, the fermentation broth of *Escherichia coli* expressing thermostable phosphoglucomutase, the fermentation broth of *Escherichia coli* expressing thermostable phosphoglucose isomerase, the fermentation broth of *Escherichia coli* expressing thermostable mannose 6-phosphate isomerase, and the fermentation broth of *Escherichia coli* expressing thermostable mannose 6-phosphate phosphatase prepared in Example 9 were mixed in a ratio of 1:1:1:1:1 according to OD600, so that the OD600=100. And 1% w/v of diatomite was added to the bacteria suspension, and stirred homogeneously. Subsequently, 0.4% w/v of the aqueous solution of polyethyleneimine having a molecular weight of 600 was added and flocculation was carried out at room temperature. Then, 0.4% v/v of epichlorohydrin aqueous solution was added and cross-linking was carried out at room temperature for 2 hours. Filtration was carried out under vacuum to obtain a filter cake. The filter cake was extruded and thus granulated into strips having a particle size of 1.0 mm with a rotary granulator. Then the strips were broken into particles having a uniform length with a spherical shot blasting machine. The resulting immobilized cell particles were subjected to drying by boiling at 70 °C to obtain immobilized cells.

Mannose was produced using the method of Example 2. Experimental results showed that when the immobilized *Escherichia col* was used to catalyze consecutive rounds of reactions, the initial product yield reached up to 61%, and as the catalysis was carried out for 25 consecutive batches, the product yield was maintained at 39%.

Comparative Example 1: Production of Mannose with *Bacillus subtilis*

The fermentation broths prepared in Example 1 were centrifuged at 5,500 rpm for 10 min. The supernatants were discarded to obtain whole cells expressing thermostable α-glucan phosphorylase, whole cells expressing thermostable phosphoglucomutase, whole cells expressing thermostable phosphoglucose isomerase, whole cells expressing thermostable mannose 6-phosphate isomerase, and whole cells expressing thermostable mannose 6-phosphate phosphatase respectively. A 50 mM sodium phosphate buffer (pH 7.5) was added to the above cells respectively to resuspend the bacterial to OD600=200. The resuspended bacterial were heated at 75 °C for 90 min. The above whole cells were mixed in a sodium phosphate buffer (pH 7.0) in a ratio of 1:1:1:1:1, so that OD600=200.

In a reaction system having a volume of 1 L, starch at a final concentration of 100 g/L, a 50 mM sodium phosphate buffer (pH 7.0) and the above mixed *Bacillus subtilis* were respectively added to achieve OD600=20. Reaction was allowed to carried out in a water bath in a shaker at 70 °C.

Figure 6:
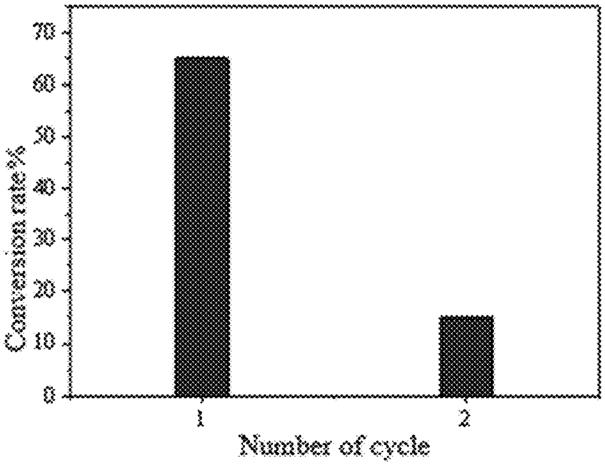
FIG. 6 shows the effect of the *Bacillus subtilis* in producing mannose in Comparative Example 1.

During reaction, the content of mannose was analyzed by HPLC. After the reaction was completed, the cells were precipitated by centrifugation, washed with a buffer and then used in reactions for the next batch. Experimental results as shown in FIG. 6 demonstrated that when the immobilized *Bacillus subtilis* were used to catalyze consecutive rounds of reactions, the initial product yield reached up to 65%, but as the catalysis was carried out for 2 consecutive batches, the product yield was lowered to only 15%.

Comparative Example 2: Production of Mannose with *Escherichia coli*

The fermentation broths prepared in Example 9 were centrifuged at 5,500 rpm for 10 min. The supernatants were discarded to obtain whole cells expressing thermostable α-glucan phosphorylase, whole cells expressing thermostable phosphoglucomutase, whole cells expressing thermostable phosphoglucose isomerase, whole cells expressing thermostable mannose 6-phosphate isomerase, and whole cells expressing thermostable mannose 6-phosphate phosphatase respectively. A 50 mM sodium phosphate buffer (pH 7.5) was added to the above cells respectively to resuspend the bacterial to OD600=200. The resuspended bacterial were heated at 75 °C for 90 min. The above whole cells were mixed in a sodium phosphate buffer (pH 7.0) in a ratio of 1:1:1:1:1, so that OD600=200.

Figure 7:
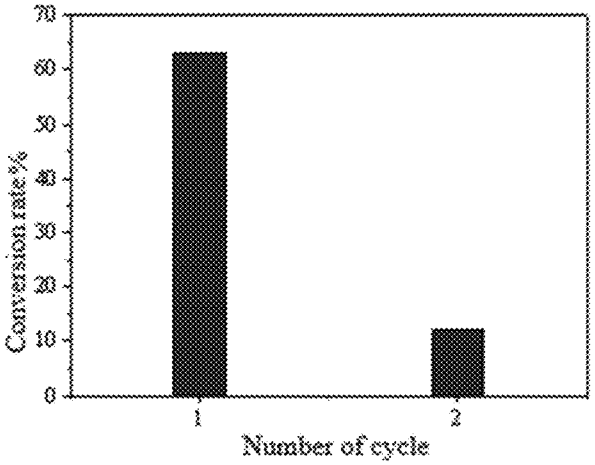
FIG. 7 shows the effect of the *Escherichia coli* in producing mannose in Comparative Example 2.

In a reaction system having a volume of 1 L, starch at a final concentration of 100 g/L, a 50 mM sodium phosphate buffer (pH 7.0) and the above mixed *Escherichia coli* were respectively added to achieve OD600=20. Reaction was allowed to carried out in a water bath in a shaker at 70 °C. During reaction, the content of mannose was analyzed by HPLC. After the reaction was completed, the cells were precipitated by centrifugation, washed with a buffer and then used in reactions for the next batch. Experimental results as shown in FIG. 7 demonstrated that when the *Escherichia coli* were used to catalyze consecutive rounds of reactions, the initial product yield reached up to 63%, but as the catalysis was carried out for 2 consecutive batches, the product yield was lowered to only 12%.

Comparative Example 3: Production of Mannose with Immobilized Permeable *Bacillus subtilis*

Recombinant *Bacillus subtilis* strains expressing a gene of thermostable α-glucan phosphorylase, a gene of thermostable phosphoglucomutase, a gene of thermostable phosphoglucose isomerase, a gene of thermostable mannose 6-phosphate isomerase, or a gene of thermostable mannose 6-phosphate phosphatase were selected respectively, inoculated into LB medium respectively, and cultured overnight at 37 °C with shaking. Then the culture was transferred to LB medium at an inoculum volume of 1%, and cultured overnight at 37 °C with shaking, centrifuged at 5,500 rpm for 10 min then with the supernatants discarded to obtain whole cells expressing thermostable α-glucan phosphorylase, whole cells expressing thermostable phosphoglucomutase, whole cells expressing thermostable phosphoglucose isomerase, whole cells expressing thermostable mannose 6-phosphate isomerase, and whole cells expressing thermostable mannose 6-phosphate phosphatase, respectively. A 50 mM sodium phosphate buffer (pH 7.5) was added to the above cells respectively to resuspend the bacteria to OD600=200. The resuspended bacteria were heated at 75 °C for 90 min.

The above permeable whole cells were mixed in a sodium phosphate buffer (pH 7.0) in a ratio of 1:1:1:1:1, so that OD600=100. And 5% w/v of diatomite was added to the bacteria suspension, and stirred homogeneously. Subsequently, 0.5% w/v of the aqueous solution of polyethyleneimine having a molecular weight of 70,000 was added and flocculation was carried out at room temperature. Then, 0.5% v/v of glutaraldehyde aqueous solution was added and cross-linking was carried out at room temperature for 2 hours. Filtration was carried out under vacuum to obtain a filter cake. The filter cake was extruded and thus granulated into particles having a particle size of 0.4 mm with a rotary granulator. The resulting immobilized cell particles were dried at 30 °C to obtain immobilized cells.

Mannose was produced using the method of Example 2. Experimental results showed that when the immobilized permeable *Bacillus subtilis* were used to catalyze consecutive rounds of reactions, the initial product yield reached up to 55%, and as the catalysis was carried out for 25 consecutive batches, the product yield was 27%.

Comparative Example 4: Production of Mannose with Immobilized Permeable *Escherichia coli*

Recombinant *Escherichia coli* strains expressing a gene of thermostable α-glucan phosphorylase, a gene of thermostable phosphoglucomutase, a gene of thermostable phosphoglucose isomerase, a gene of thermostable mannose 6-phosphate isomerase, or a gene of thermostable mannose 6-phosphate phosphatase were selected respectively, inoculated into LB medium respectively, and cultured overnight at 37 °C with shaking. Then the culture was transferred to LB medium at an inoculum volume of 1%, added with IPTG for induction at 18 °C and cultured overnight with shaking, centrifuged at 5,500 rpm for 10 min then with the supernatants discarded to obtain whole cells expressing thermostable α-glucan phosphorylase, whole cells expressing thermostable phosphoglucomutase, whole cells expressing thermostable phosphoglucose isomerase, whole cells expressing thermostable mannose 6-phosphate isomerase, and whole cells expressing thermostable mannose 6-phosphate phosphatase, respectively. A 50 mM sodium phosphate buffer (pH 7.5) was added to the above cells respectively to resuspend the bacteria to OD600=200. The resuspended bacteria were heated at 75 °C for 90 min.

The above permeable whole cells were mixed in a sodium phosphate buffer (pH 7.0) in a ratio of 1:1:1:1:1, so that OD600=100. And 1% w/v of diatomite was added to the bacteria suspension, and stirred homogeneously. Subsequently, 0.5% w/v of the aqueous solution of polyethyleneimine having a molecular weight of 70,000 was added and flocculation was carried out at room temperature. Then, 1% v/v of glutaraldehyde aqueous solution was added and cross-linking was carried out at room temperature for 2 hours. Filtration was carried out under vacuum to obtain a filter cake. The filter cake was extruded and thus granulated into particles having a particle size of 1.0 mm with a rotary granulator. The resulting immobilized cell particles were dried at 30 °C to obtain immobilized cells.

Mannose was produced using the method of Example 2. Experimental results showed that when the immobilized permeable *Escherichia coli* was used to catalyze consecutive rounds of reactions, the initial product yield reached up to 56%, and as the catalysis was carried out for 25 consecutive batches, the product yield was 26%.

The invention claimed is:

1. A method for preparing immobilized cells for mannose production, comprising the steps of:

inoculating a series of broths wherein each broth contains a recombinant *Escherichia coli* or *Bacillus subtilis* expressing one of α-glucan phosphorylase, phosphoglucomutase, phosphoglucose isomerase, mannose 6-phosphate isomerase, or mannose 6-phosphate phosphatase, to obtain a series of broths expressing each of α-glucan phosphorylase, phosphoglucomutase, phosphoglucose isomerase, mannose 6-phosphate isomerase, and mannose 6-phosphate phosphatase;

fermenting the series of broths to obtain fermentation broths comprising *Escherichia coli* or *Bacillus subtilis* expressing α-glucan phosphorylase, phosphoglucomutase, phosphoglucose isomerase, mannose 6-phosphate isomerase, and mannose 6-phosphate phosphatase, and mixing the above fermentation broths to obtain a fermentation mixture;

adding an inorganic soil to the fermentation mixture, and stirring homogeneously;

further adding a flocculant to the fermentation mixture to flocculate bacteria, and then adding a cross-linking agent for cross-linking;

filtering under vacuum to obtain a filter cake, extruding the filter cake to granulate into a strip with a rotary granulator, and then breaking into particles having a uniform length with a spherical shot blasting machine; and subjecting the resulting particles to drying by boiling to obtain the immobilized cells for mannose production.

2. The method according to claim 1, wherein:

1-10% w/v of the inorganic soil is added to the fermentation mixture;

0.1-2% w/v of the flocculant is added to the fermentation mixture to flocculate the bacteria, then 0.05-3% v/v of the cross-linking agent is added, and the cross-linking is carried out for 1-4 hours;

and the temperature at an air inlet for the drying by boiling is controlled at 60-90 °C.

3. The method according to claim 1, wherein the α-glucan phosphorylase, the phosphoglucomutase, the phosphoglucose isomerase, the mannose 6-phosphate isomerase, and the mannose 6-phosphate phosphatase are thermostable.

4. The method according to claim 3, characterized in that thermostable refers to having an enzymatic activity at 40 °C or above.

5. The method according to claim 3, characterized in that the bacteria expressing the thermostable α-glucan phosphorylase, the thermostable phosphoglucomutase, the thermostable phosphoglucose isomerase, the thermostable mannose 6-phosphate isomerase, and the thermostable mannose 6-phosphate phosphatase are mixed in a ratio of (0.1-10):(0.1-10):(0.1-10):(0.1-10):(0.1-10), and the bacteria suspension obtained by mixing has an OD600 of 10-150.

6. The method according to claim 1, characterized in that the inorganic soil is montmorillonite, diatomite, kaolin or bentonite.

7. The method according to claim 1, characterized in that the flocculant is selected from polyethyleneimine, chitosan, poly(diallyldimethylammonium chloride)(PDADMAC), or polyacrylamide.

8. The method of claim 7, characterized in that the flocculant is polyethyleneimine having a molecular weight of 600-70,000 Da, or PDADMAC.

9. The method according to claim 1, characterized in that the cross-linking agent is glutaraldehyde, tris(hydroxymethyl)phosphine, N,N-methylenebisacrylamide, or epichlorohydrin.

10. The method according to claim 1, characterized in that the method further comprises a step of sieving the obtained immobilized cells to obtain morphologically uniform immobilized cells.

11. A method for producing mannose with an immobilized cell, comprising contacting starch or a starch derivative with the immobilized cells of claim 1 to produce mannose.

12. The method according to claim 11, further comprising a step of filtering and recovering the immobilized cells after the reaction is completed.

13. The method according to claim 11, wherein the method is performed at 50-300 g/L of starch or starch derivative, in a buffer at pH 5.0-8.0, 10-50 mM inorganic phosphate, and 3-7 mM divalent magnesium ions.

14. The method according to claim 13, wherein the buffer is an HEPES buffer, a phosphate buffer, a Tris buffer, or an acetate buffer; and wherein the inorganic phosphate is sodium phosphate or potassium phosphate.

* * * * *

SEQUENCE LISTING

<160> NUMBER OF SEQ ID NOS: 20

<210> SEQ ID NO 1
<211> LENGTH: 50
<212> TYPE: DNA
<213> ORGANISM: Artificial Sequence
<220> FEATURE:
<223> OTHER INFORMATION: primer

<400> SEQUENCE: 1
agaaacaaca aagggggaga tttgtatggt gaacgtttcc aatgccgttg 50

<210> SEQ ID NO 2
<211> LENGTH: 51
<212> TYPE: DNA
<213> ORGANISM: Artificial Sequence
<220> FEATURE:
<223> OTHER INFORMATION: primer

<400> SEQUENCE: 2
gcttgagctc gactctagag gatcctcagt caagtccctt ccacttgacc a 51

<210> SEQ ID NO 3
<211> LENGTH: 51
<212> TYPE: DNA
<213> ORGANISM: Artificial Sequence
<220> FEATURE:
<223> OTHER INFORMATION: primer

<400> SEQUENCE: 3
tggtcaagtg gaagggactt gactgaggat cctctagagt cgagctcaag c 51

<210> SEQ ID NO 4
<211> LENGTH: 50
<212> TYPE: DNA
<213> ORGANISM: Artificial Sequence
<220> FEATURE:
<223> OTHER INFORMATION: primer

<400> SEQUENCE: 4
caacggcatt ggaaacgttc accatacaaa tctccccctt tgttgtttct 50

<210> SEQ ID NO 5
<211> LENGTH: 50
<212> TYPE: DNA
<213> ORGANISM: Artificial Sequence
<220> FEATURE:
<223> OTHER INFORMATION: primer

<400> SEQUENCE: 5
agaaacaaca aagggggaga tttgtatggg caaactgttt ggtaccttcg 50

<210> SEQ ID NO 6
<211> LENGTH: 50
<212> TYPE: DNA
<213> ORGANISM: Artificial Sequence
<220> FEATURE:
<223> OTHER INFORMATION: primer

<400> SEQUENCE: 6
gcttgagctc gactctagag gatccttaac ctttcagtgc ttcttccagc 50

<210> SEQ ID NO 7
<211> LENGTH: 51
<212> TYPE: DNA
<213> ORGANISM: Artificial Sequence
<220> FEATURE:
<223> OTHER INFORMATION: primer

<400> SEQUENCE: 7
gctggaagaa gcactgaaag gttaaggatc ctctagagtc gagctcaagc t 51

<210> SEQ ID NO 8
<211> LENGTH: 50
<212> TYPE: DNA
<213> ORGANISM: Artificial Sequence
<220> FEATURE:
<223> OTHER INFORMATION: primer

<400> SEQUENCE: 8
cgaaggtacc aaacagtttg cccatacaaa tctccccctt tgttgtttct 50

<210> SEQ ID NO 9
<211> LENGTH: 50
<212> TYPE: DNA
<213> ORGANISM: Artificial Sequence
<220> FEATURE:
<223> OTHER INFORMATION: primer

<400> SEQUENCE: 9
agaaacaaca aagggggaga tttgtatgct gcgtctggat actcgctttc 50

<210> SEQ ID NO 10
<211> LENGTH: 51
<212> TYPE: DNA
<213> ORGANISM: Artificial Sequence
<220> FEATURE:
<223> OTHER INFORMATION: primer

<400> SEQUENCE: 10
agcttgagct cgactctaga ggatccttaa ccagccaggc gtttacgagt c 51

<210> SEQ ID NO 11
<211> LENGTH: 51
<212> TYPE: DNA
<213> ORGANISM: Artificial Sequence
<220> FEATURE:
<223> OTHER INFORMATION: primer

<400> SEQUENCE: 11
gactcgtaaa cgcctggctg gttaaggatc ctctagagtc gagctcaagc t 51

<210> SEQ ID NO 12
<211> LENGTH: 50
<212> TYPE: DNA
<213> ORGANISM: Artificial Sequence
<220> FEATURE:
<223> OTHER INFORMATION: primer

<400> SEQUENCE: 12
gaaagcgagt atccagacgc agcatacaaa tctccccctt tgttgtttct 50

<210> SEQ ID NO 13
<211> LENGTH: 56
<212> TYPE: DNA
<213> ORGANISM: Artificial Sequence
<220> FEATURE:
<223> OTHER INFORMATION: primer

<400> SEQUENCE: 13
gtagaaacaa caaaggggga gatttgtatg aggcggttgg agcccaaacc cgtggc 56

<210> SEQ ID NO 14
<211> LENGTH: 55
<212> TYPE: DNA
<213> ORGANISM: Artificial Sequence
<220> FEATURE:
<223> OTHER INFORMATION: primer

<400> SEQUENCE: 14
ccacgggttt gggctccaac cgcctcatac aaatctcccc ctttgttgtt tctac 55

<210> SEQ ID NO 15
<211> LENGTH: 53
<212> TYPE: DNA
<213> ORGANISM: Artificial Sequence
<220> FEATURE:
<223> OTHER INFORMATION: primer

<400> SEQUENCE: 15
tgccgccctg gccaaggagg gggcgtgagg atcctctaga gtcgagctca agc 53

<210> SEQ ID NO 16
<211> LENGTH: 53
<212> TYPE: DNA
<213> ORGANISM: Artificial Sequence
<220> FEATURE:
<223> OTHER INFORMATION: primer

<400> SEQUENCE: 16
gcttgagctc gactctagag gatcctcacg ccccctcctt ggccagggcg gca 53

<210> SEQ ID NO 17
<211> LENGTH: 52
<212> TYPE: DNA
<213> ORGANISM: Artificial Sequence
<220> FEATURE:
<223> OTHER INFORMATION: primer

<400> SEQUENCE: 17
gtagaaacaa caaaggggga gatttgtatg taccgcgttt ttgtttttga tc 52

<210> SEQ ID NO 18
<211> LENGTH: 52
<212> TYPE: DNA
<213> ORGANISM: Artificial Sequence
<220> FEATURE:
<223> OTHER INFORMATION: primer

<400> SEQUENCE: 18
gatcaaaaac aaaaacgcgg tacatacaaa tctccccctt tgttgtttct ac 52

<210> SEQ ID NO 19
<211> LENGTH: 49
<212> TYPE: DNA
<213> ORGANISM: Artificial Sequence
<220> FEATURE:
<223> OTHER INFORMATION: primer

<400> SEQUENCE: 19
agcaccgatt gtctggatga atgaggatcc tctagagtcg agctcaagc 49

<210> SEQ ID NO 20
<211> LENGTH: 49
<212> TYPE: DNA
<213> ORGANISM: Artificial Sequence
<220> FEATURE:
<223> OTHER INFORMATION: primer -continued

<400> SEQUENCE: 20

```
gcttgagctc gactctagag gatcctcatt catccagaca atcggtgct          49
```